US007056722B1

(12) United States Patent
Coelho et al.

(10) Patent No.: US 7,056,722 B1
(45) Date of Patent: Jun. 6, 2006

(54) APPARATUS AND METHOD OF PREPARATION OF STABLE, LONG TERM THROMBIN FROM PLASMA AND THROMBIN FORMED THEREBY

(75) Inventors: Philip Henry Coelho, El Dorado Hills, CA (US); Phil Kingsley, Sacremento, CA (US); Jim Brausch, Sacramento, CA (US); James H. Godsey, Folsom, CA (US); Gail Rock, Ottawa (CA)

(73) Assignee: ThermoGenesis Corp., Rancho Cordova, CA (US)

( * ) Notice: Subject to any disclaimer, the term of this patent is extended or adjusted under 35 U.S.C. 154(b) by 614 days.

(21) Appl. No.: 09/709,237

(22) Filed: Nov. 10, 2000

Related U.S. Application Data

(62) Division of application No. 09/129,988, filed on Aug. 5, 1998, now Pat. No. 6,274,090.

(51) Int. Cl.
*C12N 9/74* (2006.01)
*C12Q 1/56* (2006.01)

(52) U.S. Cl. .......... 435/214; 435/13; 435/262; 435/283.1; 435/2; 422/101; 604/5; 604/246

(58) Field of Classification Search ............... 435/214, 435/2, 7.24, 177, 262, 283.1, 7.14, 13; 422/101; 604/5, 246
See application file for complete search history.

(56) References Cited

U.S. PATENT DOCUMENTS

| 1,614,532 A | 1/1927 | Mobley |
| 2,533,004 A | 12/1950 | Ferry et al. |
| 2,747,936 A | 5/1956 | Wahlin |
| 3,179,107 A | 4/1965 | Clark |
| 3,223,083 A | 12/1965 | Cobey |
| 3,236,457 A | 2/1966 | Kennedey et al. |
| 3,269,389 A | 8/1966 | Meurer et al. |
| 3,416,737 A | 12/1968 | Venus, Jr. |
| 3,467,096 A | 9/1969 | Horn |
| 3,828,980 A | 8/1974 | Creighton et al. |
| 3,942,725 A | 3/1976 | Green |
| 3,945,574 A | 3/1976 | Polnauer et al. |
| 4,040,420 A | 8/1977 | Speer |
| 4,067,333 A | 1/1978 | Reinhardt et al. |
| 4,109,653 A | 8/1978 | Kozam et al. |
| 4,265,233 A | 5/1981 | Sugitachi et al. |
| 4,298,598 A | 11/1981 | Schwarz et al. |
| 4,359,049 A | 11/1982 | Redl et al. |
| 4,362,567 A | 12/1982 | Schwarz et al. |
| 4,363,319 A | 12/1982 | Altshuler |
| 4,374,830 A | 2/1983 | Schneider |
| 4,377,572 A | 3/1983 | Schwarz et al. |
| 4,414,976 A | 11/1983 | Schwarz et al. |
| 4,427,650 A | 1/1984 | Stroetmann |
| 4,427,651 A | 1/1984 | Stroetmann |
| 4,442,655 A | 4/1984 | Stroetmann |
| 4,453,939 A | 6/1984 | Zimmerman et al. |

| 4,627,879 A | 12/1986 | Rose et al. |
| 4,631,055 A | 12/1986 | Redl et al. |
| 4,655,211 A | 4/1987 | Sakamoto et al. |
| 4,696,812 A | 9/1987 | Silbering et al. |
| 4,714,457 A | 12/1987 | Alterbaum |
| 4,734,261 A | 3/1988 | Koizumi et al. |
| 4,735,616 A | 4/1988 | Eibl et al. |
| 4,752,466 A | 6/1988 | Saferstein et al. |
| 4,767,416 A | 8/1988 | Wolf et al. |
| 4,826,048 A | 5/1989 | Skorka et al. |
| 4,842,581 A | 6/1989 | Davis |
| 4,874,368 A | 10/1989 | Miller et al. |
| 4,902,281 A | 2/1990 | Avoy |
| 4,909,251 A | 3/1990 | Seelich |
| 4,923,815 A | 5/1990 | Tanaka et al. |
| 4,965,203 A | 10/1990 | Silbering et al. |
| 4,978,336 A | 12/1990 | Capozzi et al. |
| 4,979,942 A | 12/1990 | Wolf et al. |
| 4,987,336 A | 1/1991 | L'Hermite et al. |
| 5,037,390 A | 8/1991 | Raines et al. |
| 5,089,415 A | 2/1992 | La Duca |
| 5,099,003 A | 3/1992 | Kotitschke et al. |
| 5,104,375 A | 4/1992 | Wolf et al. |
| 5,116,315 A | 5/1992 | Capozzi et al. |
| 5,130,244 A | 7/1992 | Nishimaki et al. |

(Continued)

FOREIGN PATENT DOCUMENTS

EP    0 443 724    8/1991

(Continued)

OTHER PUBLICATIONS

Fenton, II, J.W., et al., "Human Thrombins", Chemistry & Biology of Thrombin, pp. 43-70, 1977.
Rosenberg, R.D., et al., "Bovine Thrombin: Constant Specific Activity Products From Single Animals", Fed. Proc., vol. 28(2), p. 321, Abstract 361, 1969.
Quick, A.J., et al., "Production Of Thrombin From Precipitate Obtained By Acidification Of Diluted Plasma", pp. 114-118, 1955.

(Continued)

*Primary Examiner*—Chih-Min Kam
(74) *Attorney, Agent, or Firm*—Bernhard Kreten; Audrey A. Millemann

(57) ABSTRACT

A sterile method for preparing stable thrombin component from a single donor's plasma in which the thrombin component is harvested simultaneously from the clotting and adhesive proteins component from the same donor plasma in less than one hour. The combined components provide an improved biological hemostatic agent and tissue sealant by virtue of its freedom from the risk of contaminating viruses or bacteria from allogenic human or bovine blood sources. The thrombin provides polymerization of the clotting and adhesive proteins in less than five seconds, and is sufficiently stable to provide that fast clotting over a six hour period. Further, the clotting times can be predictably lengthened by diluting the thrombin with saline.

20 Claims, 12 Drawing Sheets

U.S. PATENT DOCUMENTS

| | | | |
|---|---|---|---|
| 5,143,838 A | 9/1992 | Kraus et al. | |
| 5,151,355 A | 9/1992 | Crowley et al. | |
| 5,165,938 A | 11/1992 | Knighton | |
| 5,185,001 A | 2/1993 | Galanakis | |
| 5,219,328 A | 6/1993 | Morse et al. | |
| 5,232,024 A | 8/1993 | Williams | |
| 5,290,259 A | 3/1994 | Fischer | |
| 5,290,552 A | 3/1994 | Sierra et al. | |
| 5,304,372 A | 4/1994 | Michalski et al. | |
| 5,328,462 A | 7/1994 | Fischer | |
| 5,368,563 A | 11/1994 | Lonneman et al. | |
| 5,393,666 A | 2/1995 | Linnau | |
| 5,405,607 A | 4/1995 | Epstein | |
| 5,411,885 A | 5/1995 | Marx | |
| 5,443,959 A | 8/1995 | Kikuchi et al. | |
| 5,460,945 A | 10/1995 | Springer et al. | |
| 5,474,540 A | 12/1995 | Miller et al. | |
| 5,474,770 A | 12/1995 | Broly et al. | |
| 5,476,771 A * | 12/1995 | Reid et al. | 435/13 |
| 5,480,378 A | 1/1996 | Weis-Fogh et al. | |
| 5,506,127 A | 4/1996 | Proba et al. | |
| 5,510,102 A | 4/1996 | Cochrum | |
| 5,575,779 A | 11/1996 | Barry | |
| 5,578,459 A | 11/1996 | Gordon et al. | |
| 5,585,007 A | 12/1996 | Antanavich et al. | |
| 5,591,444 A * | 1/1997 | Boss, Jr. | 424/426 |
| 5,605,887 A | 2/1997 | Pines et al. | |
| 5,614,204 A | 3/1997 | Cochrum | |
| 5,631,019 A | 5/1997 | Marx | |
| 5,643,192 A | 7/1997 | Hirsh et al. | |
| 5,648,265 A | 7/1997 | Epstein | |
| 5,674,482 A * | 10/1997 | Regan et al. | 424/78.37 |
| 5,750,657 A | 5/1998 | Edwardson et al. | |
| 5,795,571 A | 8/1998 | Cederholm-Williams | |
| 5,795,780 A | 8/1998 | Cederholm-Williams | |
| 5,804,428 A | 9/1998 | Edwardson et al. | |
| 5,965,692 A * | 10/1999 | Gustafsson et al. | 530/300 |
| 6,060,461 A | 5/2000 | Drake | |
| 6,444,228 B1 * | 9/2002 | Baugh et al. | 424/530 |

FOREIGN PATENT DOCUMENTS

| | | |
|---|---|---|
| EP | 0 505 604 | 9/1992 |
| EP | 0 534 178 | 3/1993 |
| EP | 0 592 242 | 4/1994 |
| WO | WO 86/01814 | 3/1986 |
| WO | WO 88/02259 | 4/1988 |
| WO | WO 88/03151 | 5/1988 |
| WO | WO 91/09641 | 7/1991 |
| WO | WO 93/19805 | 10/1993 |
| WO | WO 94/00566 | 1/1994 |
| WO | WO 96/17871 | 6/1996 |
| WO | WO 96/31245 | 10/1996 |
| WO | WO 99/45938 | 9/1999 |

OTHER PUBLICATIONS

Eagle, H., "Studies On Blood Coagulation", pp. 531-545, 1934.

Mann, K.G., et al., "The Molecular Weights Of Bovine Thrombin And Its Primary Autolysis Products", pp. 6555-6557, 1969.

Mann, K.G., et al., "Multiple Active Forms Of Thrombin", Biological Chemistry, vol. 246(19), pp. 5994-6001, 1971.

Martin, M., et al., "Thrombolysis In Patients With Chronic Arterial Occlusions", Thrombolytic Therapy, vol. 47, pp. 235-241, 1971.

Fenton, II, J.W., et al., "Large-Scale Preparation And Preliminary Characterization Of Human Thrombin", Biochimica et Biophysica Acta., vol. 229, pp. 26-32, 1971.

Andrianova, I.G., et al., "A Simple Method For Simultaneously Obtaining Pure Fibrinogen And Thrombin From Blood Plasma", Lab Delo, vol. 11, pp. 648-650, 1975. (Plus English translation).

Georgi, M., et al., "Occlusion Of The Renal Artery By Intra-Arterial Injection Of Thrombin In A Case Of Inoperable Renal Tumor", Deutsche Medizinische Wochenschrift, vol. 100(47), pp. 2428-2429, 1975. (Plus English translation).

Lundblad, R.L., et al., "Preparation And Partial Characterization Of Two Forms Of Bovine Thrombin", Biochemical and Biophysical Research Communications, vol. 66(2), pp. 482-489, 1975.

Sakuragawa, N., et al., "Purification And Some Characterization Of Human Thrombin", Acta Medica et Biologica, vol. 23(1), pp. 65-73, 1975.

Fenton, II, J.W., et al., "Human Thrombins: Production, Evaluation, And Properties Of α-Thrombin", The Journal of Biological Chemistry, vol. 252(11), pp. 3587-3598, 1977.

Nordenman, B., et al., "Purification Of Thrombin By Affinity Chromatography On Immobilized Heparin", Thrombosis Research, vol. 11, pp. 799-808, 1977.

Nowotny, R., et al., "Mechanical Properties Of Fibrinogen-Adhesive Material", Biomaterials 1980, vol. 3, pp. 677-682, 1982.

Kotelba-Witkowska, B., et al., "Cryopreservation Of Platelet Concentrates Using Glycerol-Glucose", Transfusion, vol. 22(2), pp. 121-124, 1982.

Redl, H., et al., "Fibrin Sealant-Antibiotic Mixture—Stability And Elution Behavior", Fibrinkleber Orthop. Traumatol. Orthop. Symp., vol. 1, pp. 178-181, 1982. (Plus English translation).

Redl, H., et al., "In Vitro Properties Of Mixtures Of Fibrin Seal And Antibiotics", Biomaterials, vol. 4(1), pp. 29-32, 1983.

Gestring, G., et al., "Autologous Fibrinogen For Tissue-Adhesion, Hemostasis And Embolization", Vascular Surgery, vol. 17, pp. 294-304, 1983.

Wolf, G., "The Concentrated Autologous Tissue Glue", Archives of Oto-Rhino-Laryngology, vol. 237, pp. 279-283, 1983.

Tsvetkov, T.S., et al., "A Method For Preparation Of Dry Thrombin For Topical Application", Cryobiology, vol. 21(6), pp. 661-663, 1984.

Yu, X.J., et al., "Affinity Chromatography Of Thrombin On Modified Polystyrene Resins", Journal of Chromatography, vol. 376, pp. 429-435, 1986.

Fischer, A.M., et al., "Thrombin Purification By One-Step Preparative Affinity Chromatography On Modified Polystyrenes", Journal of Chromatography, vol. 363(1), pp. 95-100, 1986.

Harpel, P.C., "Blood Proteolytic Enzyme Inhibitors: Their Role In Modulating Blood Coagulation And Fibrinolytic Enzyme Pathways", pp. 219-234, date unknown.

Fenton, II, J.W., "Regulation Of Thrombin Generation And Functions", Seminars in Thrombosis and Hemostasis, vol. 14(3), pp. 234-240, 1988.

Awano, K., et al., "Role Of Seratonin, Histamine, And Thromboxane A2 In Platelet-Induced Contractions Of Coronary Arteries And Aortae From Rabbits", Journal Of Cardiovascular Pharmacology, vol. 13(5), pp. 781-792, 1989.

Mulvihill, J.N., et al., "Thrombin Stimulated Platelet Accumulation On Protein Coated Glass Capillaries: Role Of Adhesive Platelet a-Granule Proteins", Thrombosis and Haemostasis, vol. 62(3), pp. 989-995, 1989.

Suzuki, S., et al., "A Study On The Properties Of Commerical Thrombin Preparations", Thrombosis Research, vol. 53(3), pp. 271-277, 1989.

Ronfard, V., et al., "Use of Human Keratinocytes Cultured On Fibrin Glue In The Treatment Of Burn Wounds", Burns, vol. 17(3), pp. 181-184, 1991.

Brennan, M., "Fibrin Glue", Blood Reviews, vol. 5, pp. 240-244, 1991.

DePalma, L., et al., "The Preparation Of Fibrinogen Concentrate For Use As Fibrin Glue By Four Different Methods", Transfusion, vol. 33(9), pp. 717-720, 1993.

McCarthy, P.M., "Fibrin Glue In Cardiothoracic Surgery", Transfusion Medicine Reviews, vol. 7(3), pp. 173-179, 1993.

Cederholm-Williams, S., "Benefits Of Adjuvant Fibrin Glue In Skin Grafting", The Medical Journal of Australia, vol. 161(9), p. 575, 1994.

Cederholm-Williams, S.A., "Autologous Fibrin Sealants Are Not Yet Available", The Lancet, vol. 344(8918), p. 336, 1994.

Szczepanski, M., et al., "Thrombin Clotting Time and Fibrin Polymerization in Liver Cirrhosis", Materia Medica Polona, vol. 3(90), pp. 87-90, 1994.

Wiegand, D.A., et al., "Assessment Of Cryoprecipitate-Thrombin Solution for Dural Repair", Head & Neck, pp. 569-573, 1994.

* cited by examiner

APPARATUS AND METHOD OF PREPARATION OF STABLE, LONG TERM THROMBIN FROM PLASMA AND THROMBIN FORMED THEREBY

This application is a divisional of U.S. application Ser. No. 09/129,988, filed Aug. 5, 1998, now U.S. Pat. No. 6,274,090.

FIELD OF THE INVENTION

The following invention relates generally to the preparation of thrombin enzyme from a given unit of plasma, which is sufficiently stable that it provides rapid clotting of a fibrinogen-rich solution of clotting and adhesive proteins for more than six hours.

BACKGROUND OF THE INVENTION

Formulation of a fibrin sealant mimics the last step of the coagulation cascade wherein the enzyme thrombin cleaves fibrinogen which is then cross-linked into a semi-rigid or flexible fibrin clot. This fibrin clot adheres to wound sites, forming a barrier to fluid leaks and generates adhesion between tissues, while providing hemostatic and healing properties to the treated site.

Presently marketed, applicant's CryoSeal™ system is a device which harvests cryoprecipitated, concentrated clotting and adhesive proteins, including fibrinogen and Factor XIII from a donor's plasma in approximately one hour. The one hour cryoprecipitation harvesting, provided by the CryoSeal™ system, compared to the 1 to 2 day cryoprecipitation process routinely practiced in Blood Banks, means that CryoSeal™ harvesting of clotting and adhesive proteins can occur right in the perioperative theater with the patient close by, thereby avoiding the need to initiate the process days in advance.

These CryoSeal™ harvested clotting and adhesive proteins, when combined with bovine or human thrombin, forms a biological glue useful for surgical hemostasis and tissue adhesion. Commercially available thrombin, however, is generally sourced from bovine or human plasma pools, so the patient would still be at risk of negative immune reactions or contamination by infectious blood born viruses and, possibly Crutzfeld-Jacobs Disease (CJD) or new variants of CJD (NVCJD). An advantage of the CryoSeal™ cryoprecipitation invention is that the harvested clotting and adhesive proteins sourced from the patient's own blood eliminates the risk of contamination by infectious blood-born disease when these clotting and adhesive proteins are topically applied to the patient's surgical wound sites.

It has long been understood, however, that the safest condition for a surgical patient would result from a two component biological sealant preparation in which the thrombin component would be harvested from the same donor in which the clotting and adhesive protein component was harvested—forming a fully autologous biological sealant or glue.

For instance, Cederholm-Williams PCT Patent (WO94/00566-6 Jan. 1994) clearly describes an improved fibrin glue in which the thrombin component whose preparation method,—adjusting the ionic strength of the blood and pH of the plasma to cause precipitation of a thrombin component for later resolubalization—was described therein, would be combined with a fibrinogen component also sourced from the plasma of the same donor. These steps are so time consuming they become impractical for use in the perioperative theater where processing times should be less than one hour.

Three years later, in 1997, Hirsh, et al. (U.S. Pat. No. 5,643,192) follows the lead of Cederholm-Williams by also teaching a method of preparing fibrin glue in which both the fibrinogen and thrombin components of a fibrin glue are sourced from the same donor's plasma. The Hirsh patent describes a method of preparing thrombin in which the fibrinogen in the plasma is first precipitated to prepare a supernatant and then clotting the residual fibrinogen in the supernatant which is different than the method taught by Cederholm-Williams, but does not result in a commercially useful thrombin in that (see FIG. 1 of Hirsh, et al.) the thrombin provides clotting times of five seconds or less for only 4 minutes, and less than 10 seconds for only 47 minutes.

These clotting times are unsuitable to the needs of surgeons who could not plan their entire surgeries around the limitations of the Hirsh, et al. fibrin glue.

These clotting speeds are unsuitable to the needs of surgeons who could not plan their entire surgeries around the limitations of the Hirsh, et al. fibrin glue.

Surgeons predominately require a fast acting clotting time (<5 seconds) for hemostasis and tissue sealing or adhesion. Slow clotting biological glues (>5 seconds) will often be transported away from the wound site by oozing and bleeding before they can perform their function. A surgeon utilizing the Hirsh fibrin glue would be required to arrange his surgery so that the hemostasis and tissue sealing intended for treatment with the Hirsh fibrin glue would occur within the 4 minute window where the clotting time was less than 5 seconds, making the Hirsh invention totally impractical for most surgeries which predominantly require rapid hemostasis and tissue adhesion throughout the surgery, the time span of which could extend to six hours.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
|---|---|---|
| U.S. PATENT DOCUMENTS | | |
| 5,648,265 | Jul. 15, 1997 | Epstein |
| 5,510,102 | Apr. 4, 1996 | Cochrum |
| 5,585,007 | Dec. 17, 1996 | Antanavich, et al. |
| 5,605,887 | Feb. 25, 1997 | Pines, et al. |
| 5,614,204 | Mar. 25, 1997 | Cochrum |
| 5,631,019 | May 20, 1997 | Marx |
| 5,643,192 | Jul. 1, 1997 | Hirsh, et al. |
| FOREIGN PATENT DOCUMENTS | | |
| WO 94/00566 | Jan. 6, 1994 | Cederholm-Williams, et al. |
| EU 0 592 242 A1 | Apr. 13, 1994 | E. R. Squibb & Sons |

The other prior art listed above, not all of which are specifically discussed catalog the prior art of which the applicant is aware. These undiscussed references diverge even more starkly from the instant invention specifically distinguished below.

SUMMARY OF THE INVENTION

The instant invention addresses the long felt need for a simple, practical, fast method of preparing stable human thrombin from a donor's blood, which will provide fast clots (<5 seconds) throughout a lengthy surgery (e.g. six hours) to combine with the clotting and adhesive proteins harvested and concentrated from the same unit of blood to form a biological sealant with no patient exposure to microbial or possible CJD or NVCJD contaminations. Previous works in the field (Hirsch, et al.) exemplified a thrombin with minimal stability in that the thrombin achieved rapid clotting of fibrinogen (i.e., less than 5 seconds) during only a very narrow four to five minute time period, totally impractical for the broad range of surgeries.

The present invention provides a stable thrombin enzyme which can cause precise, repeatable fast or slow polymerization of clotting and adhesive proteins over a duration of up to six hours—throughout even a long surgery. Further, the use of clotting and adhesive proteins and thrombin all sourced from a single donor will eliminate various disease risks posed from the use of commercial fibrin glues where the fibrinogen is sourced from plasma pooled from thousands of donors and the thrombin is either sourced from a similar pool of human plasma or of bovine origin. The speed and simplicity of the production of stable thrombin by use of this invention allows it to be prepared just prior to or during operative procedures and it will provide fast clotting throughout even the longest surgeries. The thrombin produced by this invention can be diluted in saline to provide precise, slower clotting times thereby allowing any preferred time from less than four seconds to longer than 2 minutes.

The procedure of the invention is comprised of three steps, the first two of which should occur at the same time:

1. Preparing a fraction enriched in prothrombin by use of Ethanol to substantially enhance the concentration of prothrombin and at the same time remove or denature naturally occurring ingredients within plasma, such as Thrombinodulin and Antithrombin III which can bind to, block, interfere with or inhibit prothrombin or its subsequent activation to long-term functional thrombin.

2. Adding calcium ions to the enriched prothrombin solution and briefly agitating the solution to convert the pro-thrombin to stable, long term thrombin.

3. Expressing the thrombin solution through a filter to remove particulate matter which would prevent spraying the thrombin through a small orifice or expressing the thrombin through a thin tube onto a wound site.

OBJECTS OF THE INVENTION

Accordingly, it is a primary object of the present invention to provide a new and novel apparatus and method to derive fast acting, stable autologous thrombin from the donor's plasma.

It is a further object of the present invention to provide thrombin as characterized above which has a shelf life longer than most associated surgical procedures.

It is a further object of the present invention to provide thrombin as characterized above in which the clotting time can be predictably lengthened at will through dilution with saline.

It is a further object of the present invention to provide thrombin as characterized above which has simple preparatory procedures.

It is a further object of the present invention to provide a method for producing thrombin as characterized above which has a process time of less than thirty minutes.

It is a further object of the present invention to provide thrombin which can be sprayed through small orifices or expressed through thin tubes.

Viewed from a first vantage point it is the object of the present invention to provide a novel and practical method for producing stable human thrombin from a prothrombin fraction which has been substantially enriched by ethanol fractionation to increase the prothrombin concentration and at the same time remove contaminating proteins. The addition of calcium chloride to the enriched prothrombin converts prothrombin to thrombin. From the same sole donor plasma, clotting and adhesive proteins are simultaneously obtained by other means to comprise the second component necessary for the autologous biological sealant.

The present invention provides a method and apparatus that produces thrombin which is sufficiently stable that it can provide less-than-5-second clots for up to six hours, substantially more stable than demonstrated in all prior art. Further, the clot time can be modified at will through dilution with saline.

The present invention further provides an efficient method of preparation. Improved cryoprecipitation of clotting and adhesive proteins through the CryoSeal™ invention requires less than one hour. In this same time frame, the autologous human thrombin component can be manufactured with minimal materials and methods from the same source plasma. Both of the biological components of the biological glue are easily combined in a surgical setting, administered to the very same donor patient, and the resultant clotting provides hemostasis or tissue adhesion at the wound site.

The present invention additionally provides a method for sterile production of both components of the biological glue. The improved sterile manufacturing described herein provides a final product that is essentially free of contamination by non autologous microbes.

These and other objects will be made manifest when considering the following detailed specification when taken in conjunction with the appended drawing figures.

DESCRIPTION OF PREFERRED EMBODIMENTS

Figure 1:
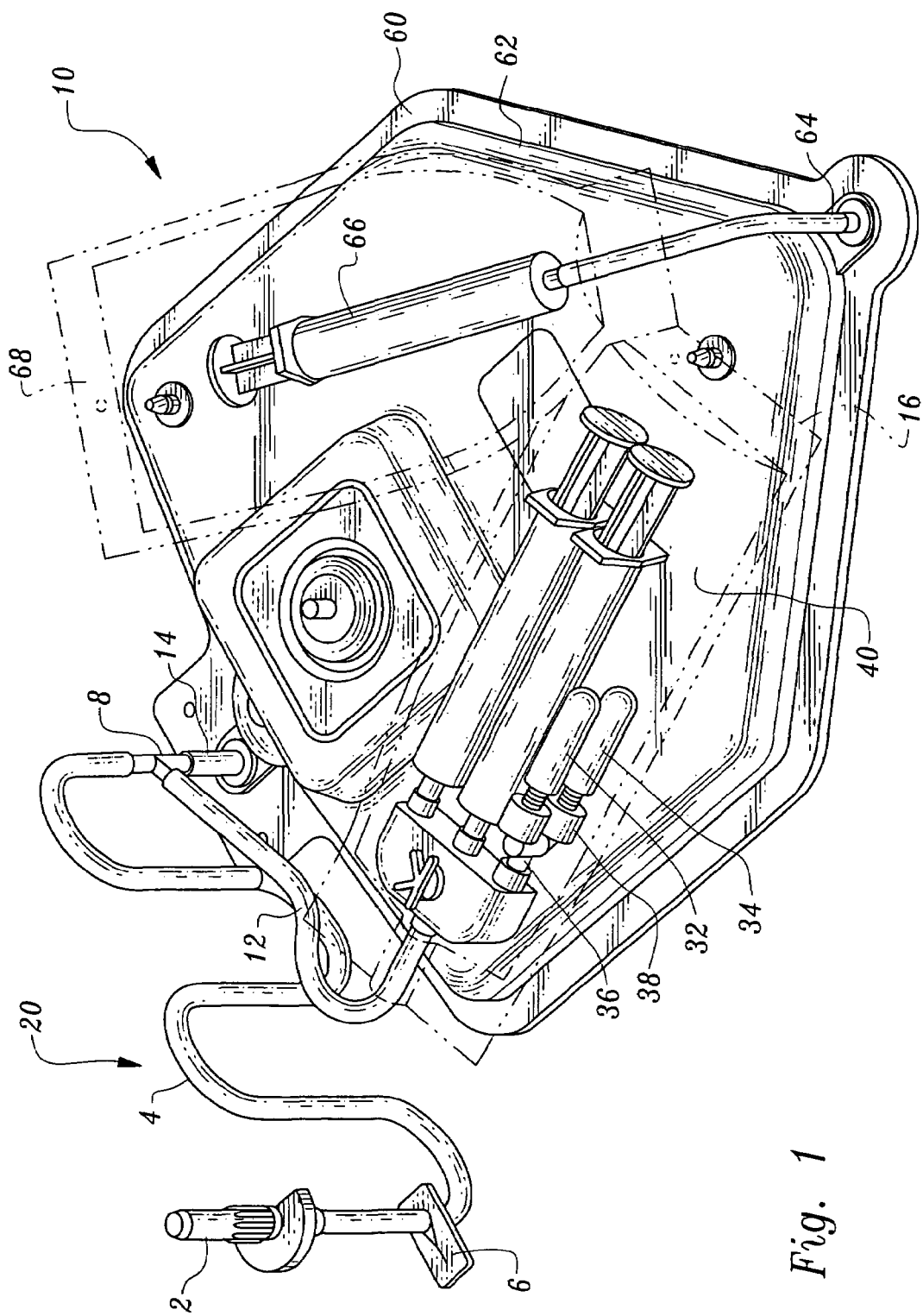
FIG. 1 is a perspective view of an apparatus for sequestering prothrombin from plasma, processing the prothrombin into thrombin and taking the plasma not relegated towards the prothrombin and extracting clotting and adhesive proteins therefrom.

Referring to the drawings, wherein like elements denote like parts throughout, reference numeral 10 is directed to the processing set according to the present invention and shown in FIG. 1.

In its essence, the processing set 10 includes a fluid receiving system 20 which communicates with both a thrombin processing unit 40 and a clotting and adhesive proteins processing unit 60.

More particularly, the fluid receiving system 20 includes an inlet 2 communicating with tubing 4 through which plasma will enter the processing units 40, 60. The conduit 4 has a stop valve 6 which can occlude the tubing 4 preventing fluid's through passage. The tubing 4 communicates through a T fitting 8 to divide plasma into two branches, a first branch 12 which leads to the thrombin processing unit 40 and a second branch 14 leading to the clotting and adhesive proteins processing unit 60.

Figure 2:
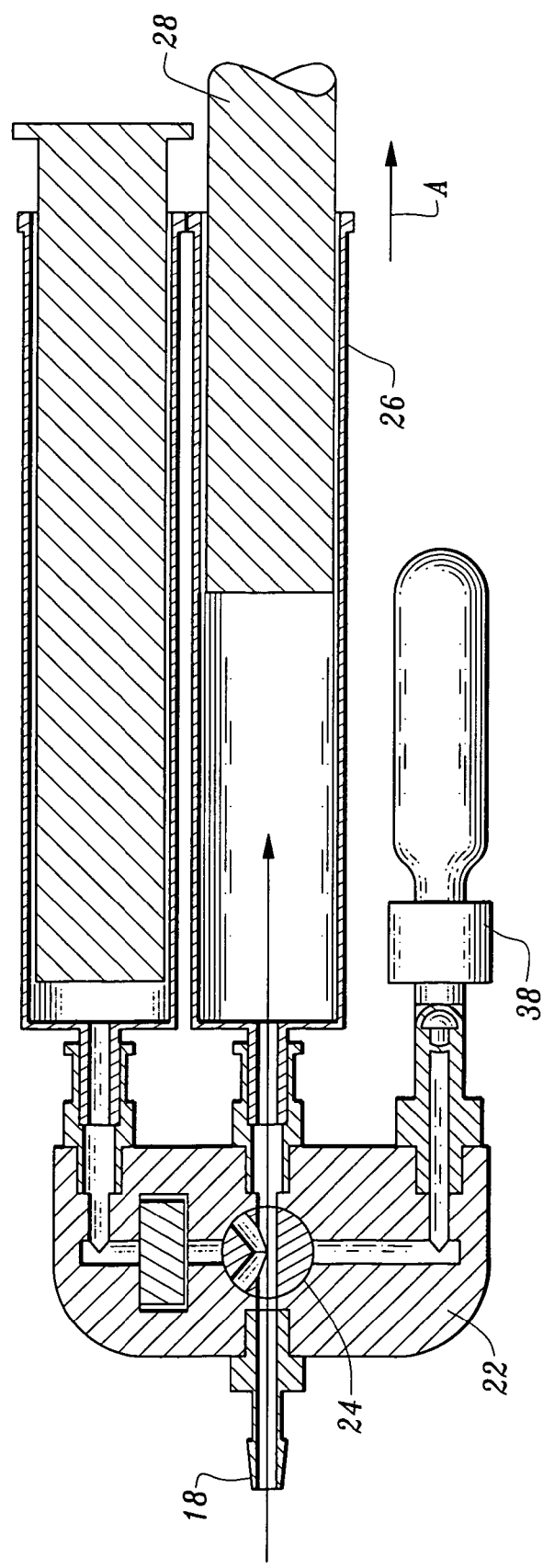
FIG. 2 is a sectional view of the thrombin processing unit where plasma is being admitted into a mixing syringe.

Since it is preferred that the blood product admitted to the inlet 2 be plasma, the whole blood is first processed either by filtering, centrifugation, or another means of settling to remove the heavier red blood cells from the blood products, leaving plasma therebeyond for use in the FIG. 1 device. The plasma required for the thrombin processing unit is preferably 8 ml. so that the final volume of concentrated thrombin matches a typical yield of cryoprecipitated clotting and adhesive proteins from the clotting and adhesive proteins processing unit 60. Referring to FIG. 2, a sealed bag 16 overlies the thrombin processing unit 40 to provide sterility until the thrombin storage syringe is introduced into a sterile surgical field. Prior to that, the thrombin processing unit is operated as shown in FIG. 2 within the sealed bag which is flexible and sized to preferably permit the movement of the syringes' plungers from the exterior of the bag. Fluid from the first branch 12 passes beyond a coupling 18 and into a manifold 22. The manifold 22 is equipped with a valve 24 that initially is directed to a mixing syringe 26 preferably formed from glass and capable of receiving a volume as great as 15 ml. The mixing syringe 26 includes a plunger 28, which when moved in the direction of the arrow A, draws the plasma from the passageway 12 and into the interior of the mixing syringe 26.

Figure 3:
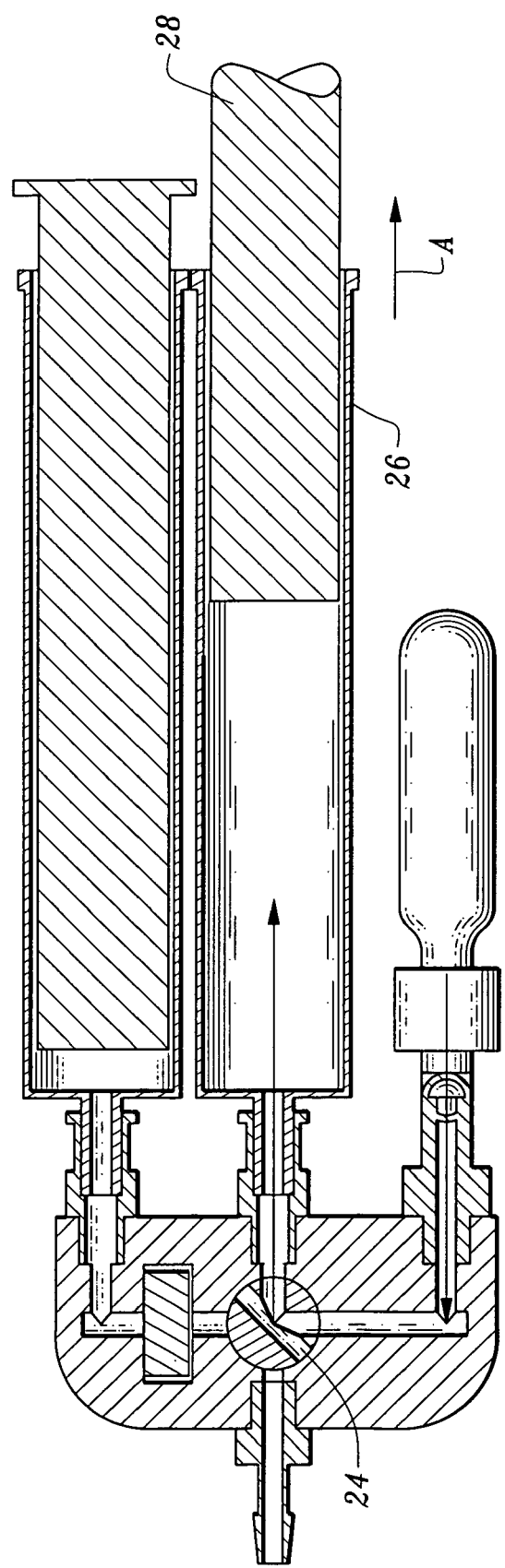
FIG. 3 is a view similar to FIG. 2 in which the processing reagents are directed to the mixing syringe for processing the plasma into prothrombin and then thrombin.

Referring to FIG. 3, the valve 24 is reoriented so that access can be gained between the mixing syringe 26 and the reagents found in ampoules 32, 34, each of which are operatively connected to the manifold 22 via a Y coupling 36 shown in FIG. 1. Access to the interior of either ampoule 32 or 34 can be had by squeezing the ampoule to rupture a frangible diaphragm. Alternatively, the intake 38 which receives the ampoule can be provided with a hollow spike which penetrates the diaphragm. In either event, the contents of both of the ampoules 32, 34 are received in the mixing syringe 26 by further retraction of the plunger 28 along the arrow A shown in FIG. 3. A first ampoule 32 is preferably provided with 2 mL of ethanol providing an EtOH concentration in the final volume of 13.6% and the second ampoule 34 is preferably provided with 1 mL calcium chloride providing a concentration in the final volume of 0.023 μM. Alternatively, these reagents contained within the two ampoules 32, 34 can be premixed into a single ampoule and dispensed simultaneously. In one form of the invention, it is possible to introduce the ethanol first, then agitate the mixing syringe 26 and then follow with the calcium chloride, but the introduction of both simultaneously to the plasma are optimally combined, followed by brief agitation.

Figure 4:
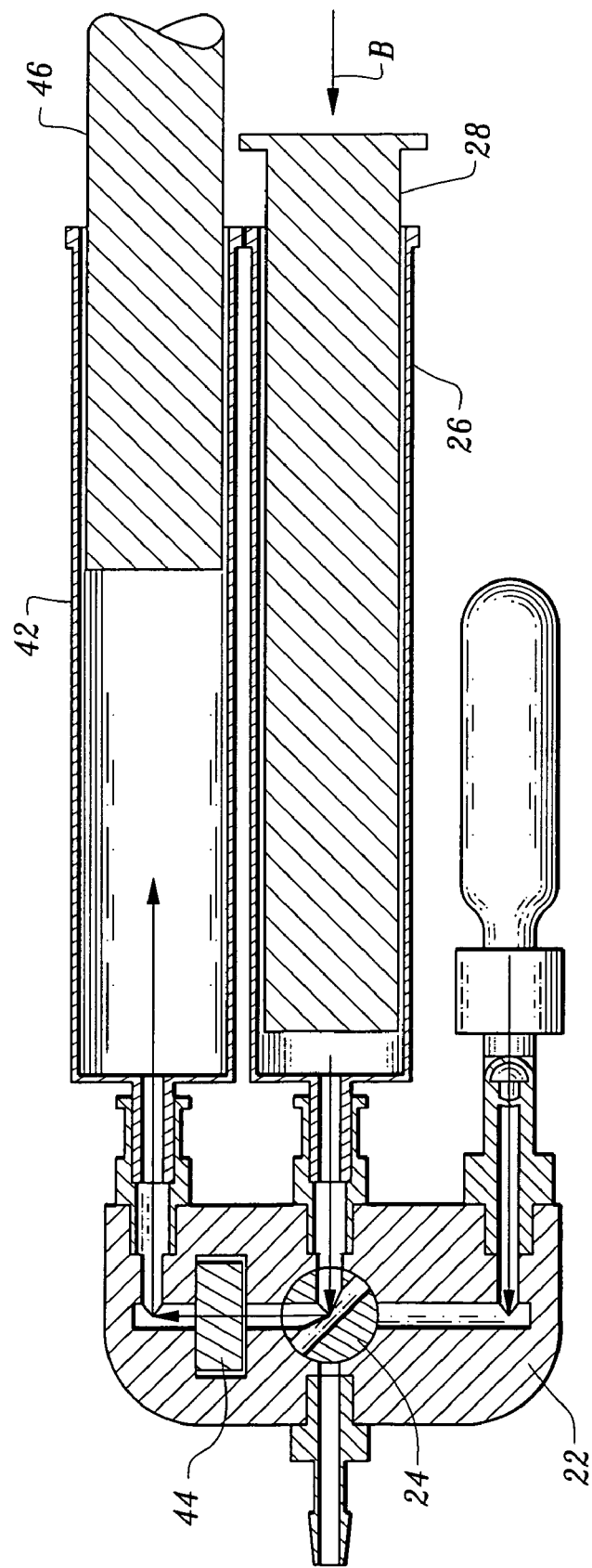
FIG. 4 is a view similar to FIGS. 2 and 3 where the thrombin is directed to a dispensing syringe after have first been filtered for particulate matter which could interfere with the thrombin being sprayed through a small orifice or expressed through a thin tube.

Once the ethanol and calcium chloride have been introduced into the mixing syringe 26, the valve 24 is reoriented so that the mixing syringe 26 is isolated. The contents are briefly agitated and allowed to incubate for about 20 minutes. Prior to pushing the contents out of the mixing syringe 26, the valve 24 is reoriented as shown in FIG. 4 after which the plunger 28 is moved in the direction of the arrow B of FIG. 4. Because the valve 24 is now set to allow communication to the thrombin dispensing syringe 42, the contents within the mixing syringe 26 will be transferred from the mixing syringe 26 to the dispensing syringe 42. More specifically, the manifold 22 includes a recess within which a filter 44 is provided in the flow path between the mixing syringe 26 and the thrombin dispensing syringe 42. Particulate matter will be retained within the filter 44 prior to delivery of the thrombin to the dispensing syringe 42. Note that as fluid enters the dispensing syringe 42, the dispensing syringe plunger 46 moves in a direction opposite arrow B.

Referring back to FIG. 1, attention is now directed to the clotting and adhesive protein processing unit 60. All of the plasma not diverted to the thrombin processing unit 40 is admitted to an interior chamber 62 of the clotting and adhesive protein processing unit 60. The clotting and adhesive protein processing unit 60 is manipulated by heat exchange and rotation so that all clotting and adhesive proteins extracted from the plasma will sediment at a nose 64 of the bag 62 for subsequent extraction by means of a clotting and adhesive protein dispensing syringe 66 contained in a sterile pouch 68. Once the thrombin has been loaded into the dispensing syringe 42, and the clotting and adhesive proteins have been loaded into the clotting and adhesive dispensing syringe 66, the two syringes can be decoupled from the processing set 10 and ganged together for spraying or line and dot application. Mixing the thrombin with the clotting and adhesive proteins forms the biological glue.

Both dispensing syringes should be stored at or below 4° C. prior to usage.

Figure 5:
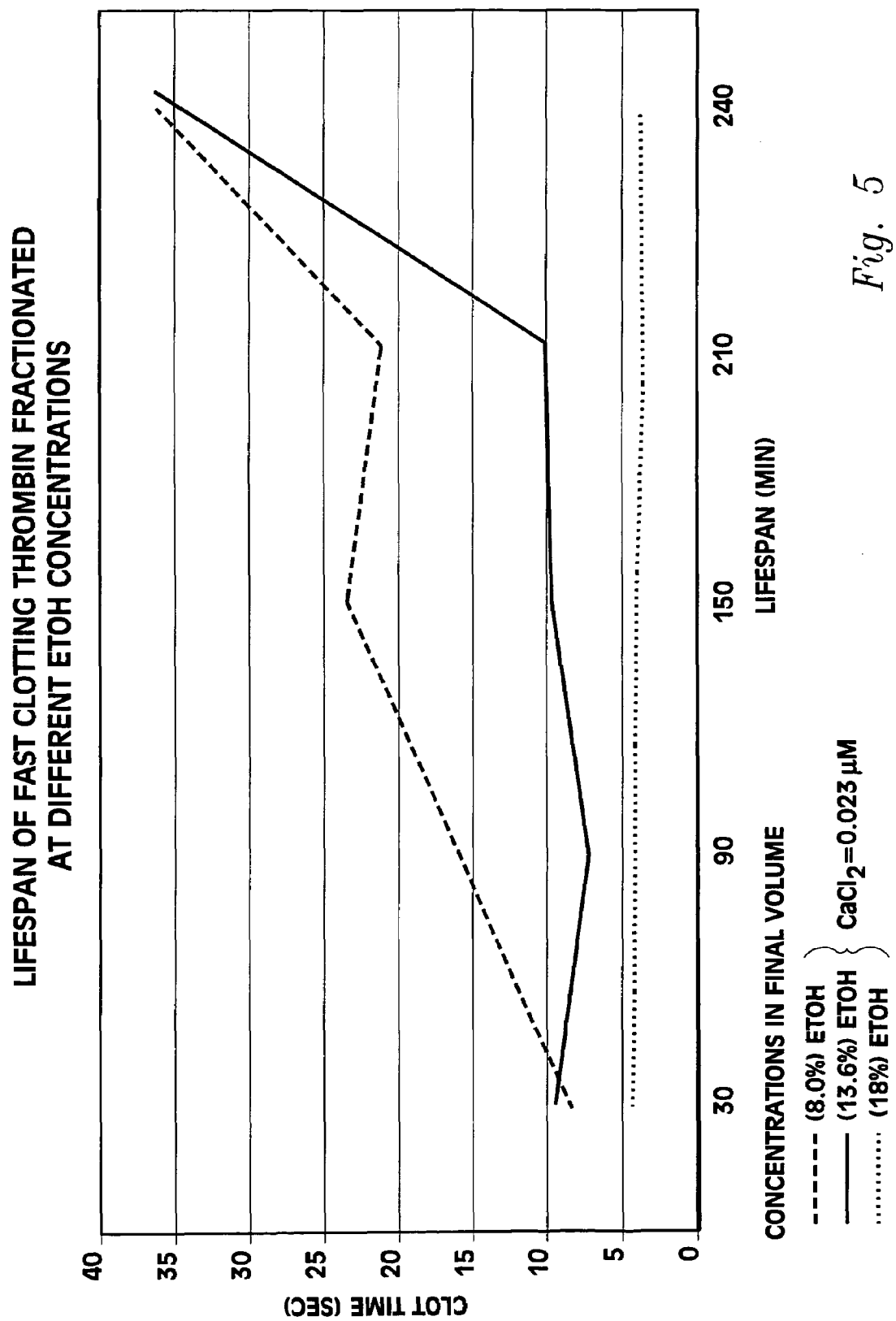
FIG. 5 is a chart illustrating the effect of various EtOH concentrations in the final volume on the life span of fast clotting thrombin when the $CaCl_2$ is held constant at 0.023 µM.

Turning to FIG. 5, a graph is shown which illustrates how ethanol concentrations alter the life span of fast clotting thrombin where the calcium chloride content is held constant at 0.023 μM. Note that at approximately 13.6% ethanol, its life span is shown to have been optimized and extend at least 240 minutes while its clotting time is substantially constant at under 5 seconds. The range between 8% and 18%, however, has utility.

Figure 6:
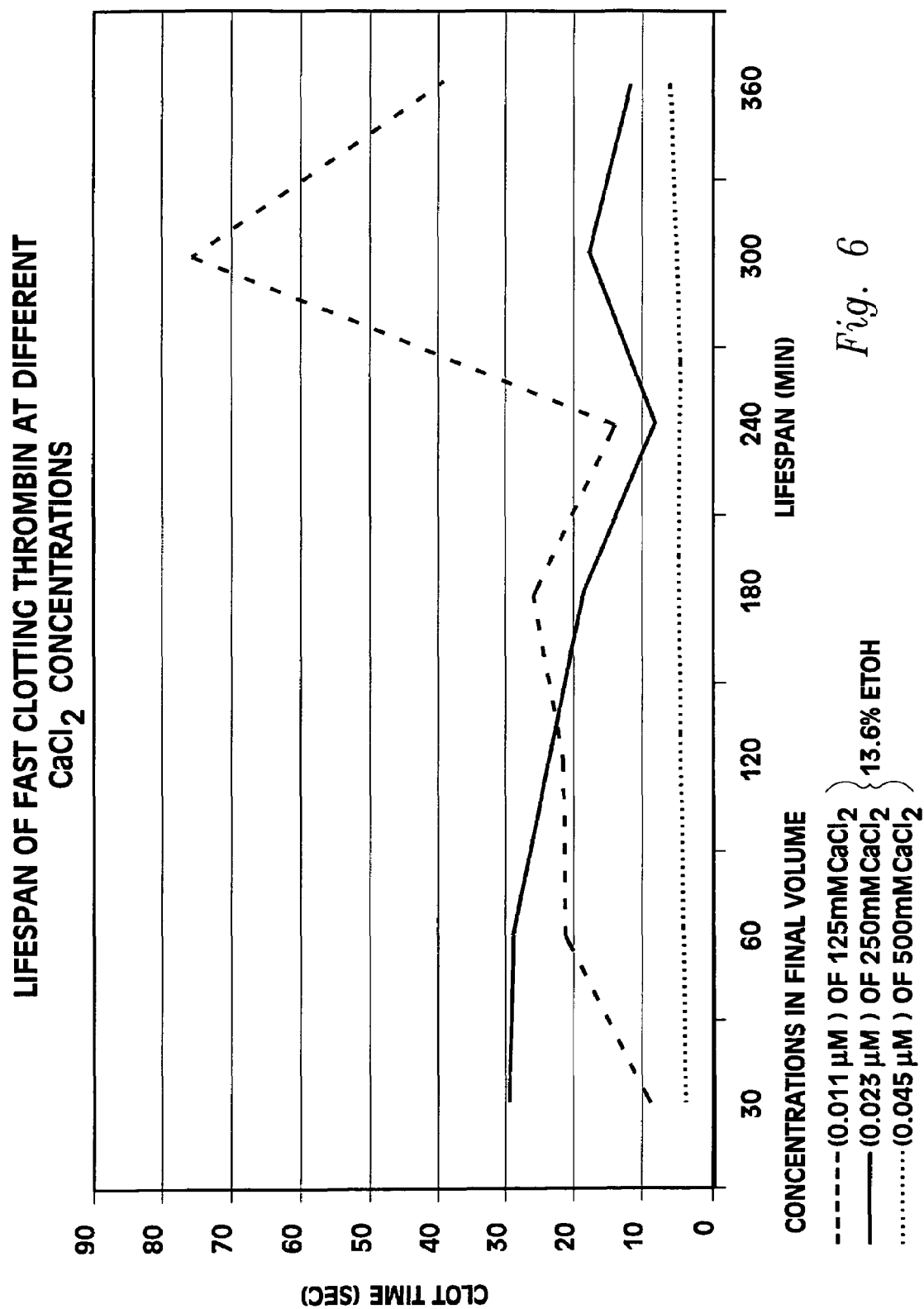
FIG. 6 is a chart illustrating the effect of various $CaCl_2$ concentrations in the final volume on the life span of fast clotting thrombin when the EtOH concentration is held constant at 13.6%.

FIG. 6 varies the calcium chloride concentration in the thrombin while the ethanol is held constant at 13.6%. As shown, the thrombin life span where the final calcium chloride concentration is at 0.023 µM of 250 mM calcium chloride appears optimized and extends to 360 minutes while maintaining a clot time under 5 seconds. The range between 0.011 µM of 125 mM and 0.045 µM of 500 mM, however, has utility.

Figure 7:
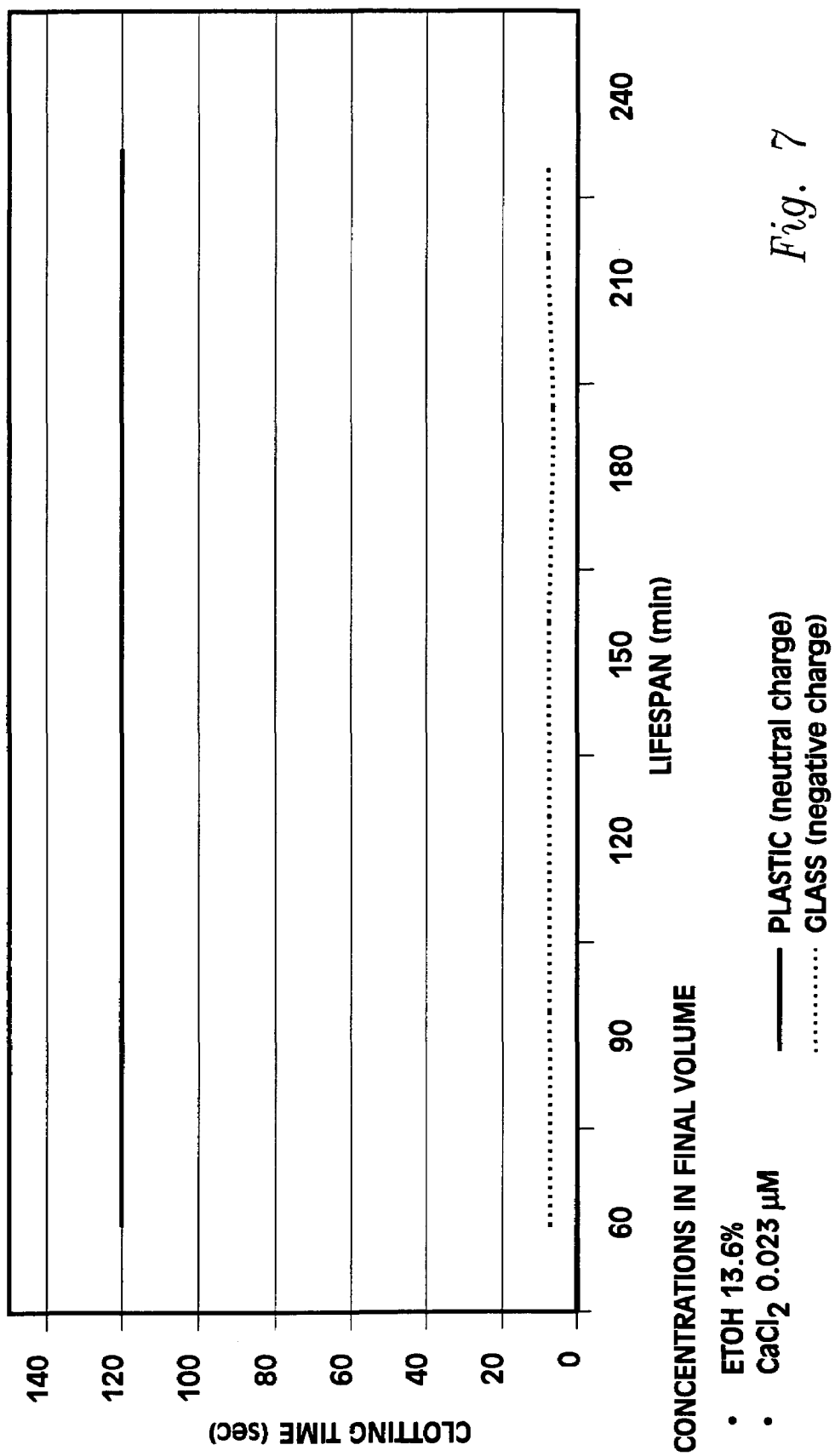
FIG. 7 is a chart illustrating that the processing of the thrombin should occur in a glass syringe for a fast clotting preparation.

FIG. 7 reflects the differences in processing the thrombin where the thrombin mixing syringe 26 is formed from glass versus plastic. As can be shown, the speed of clotting is held to close to 5 seconds or less with a life span of 60 to 240 minutes in glass.

Figure 8:
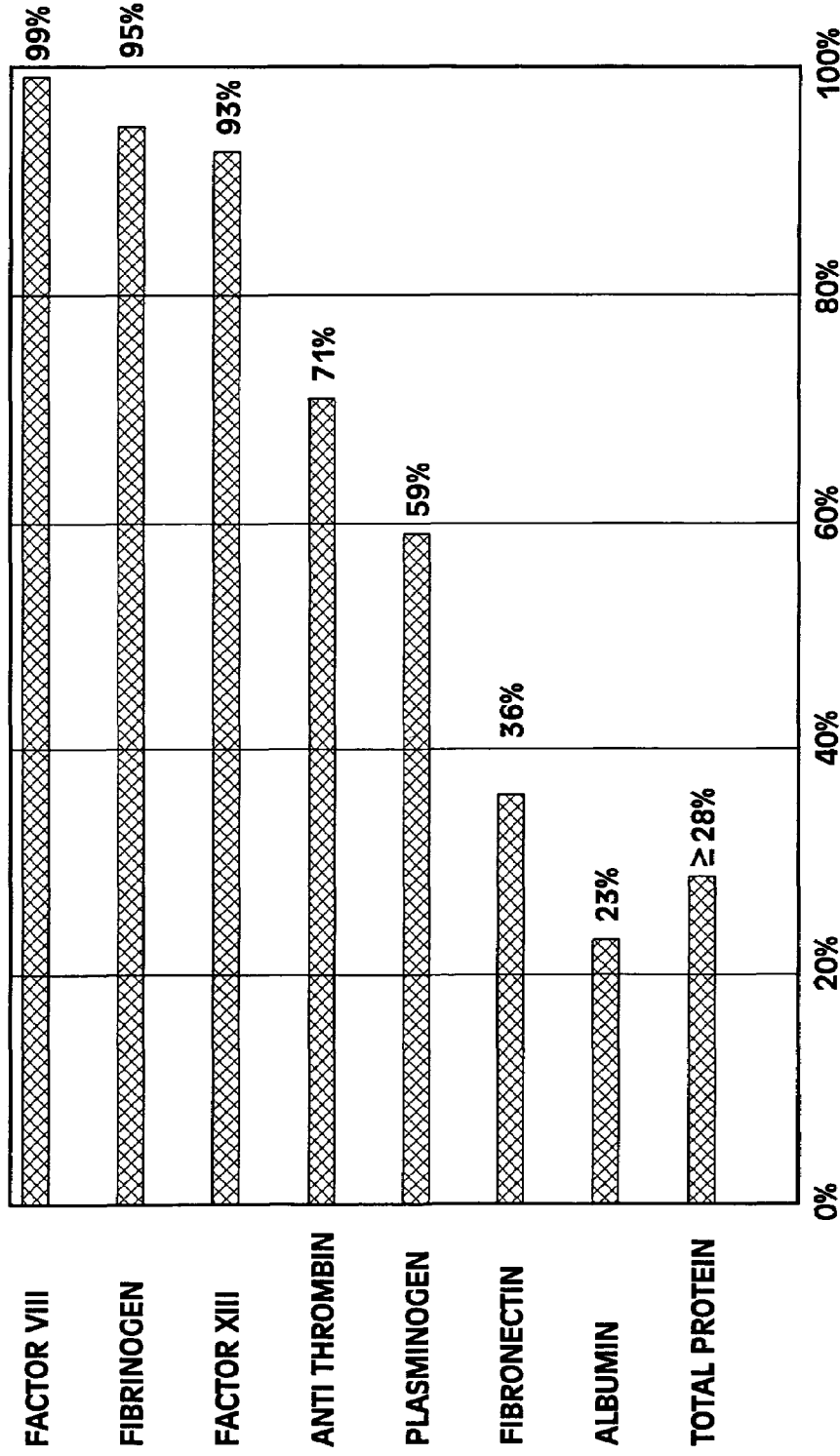
FIG. 8 is a chart describing the contaminating proteins removed from the enriched thrombin fraction after mixture with EtOH, (13.6% in final volume) and $CaCl_2$ (0.023 μM in final volume) and filtered for particulate matter.

FIG. 8 reflects the effect of using ethanol at 13.6% and calcium chloride at 0.023 µM to reduce proteins which alter the clot time of the thrombin as compared to the original plasma. As can be seen in this graph, the major interfering proteins are so efficiently removed, that the clotting time of the thrombin is not only enhanced, but held substantially stable and constant.

Figure 9:
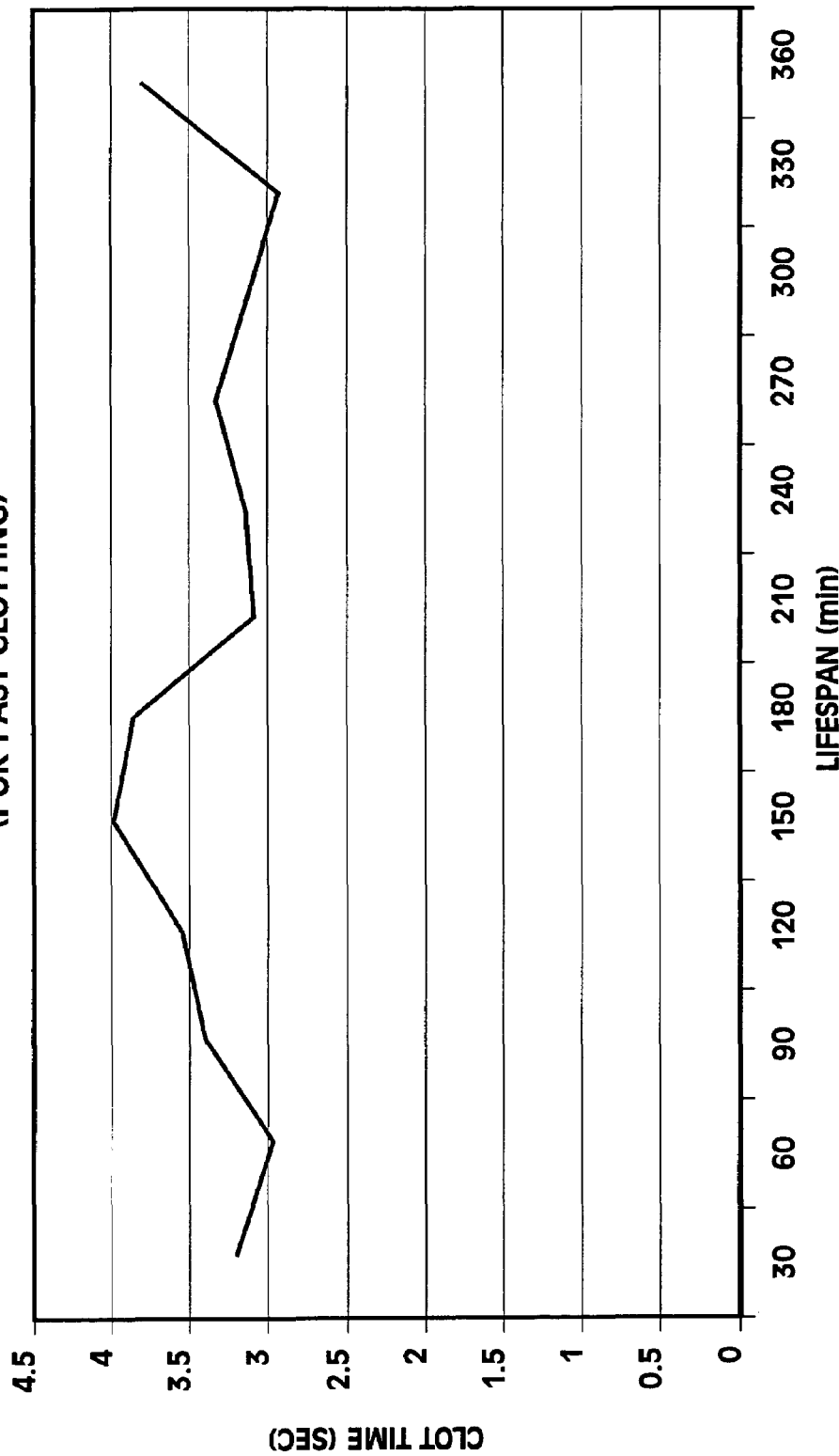
FIG. 9 is a view showing the life span of optimized thrombin preparation for fast clotting.

FIG. 9 shows in greater detail than that which is shown in FIGS. 5 and 6 regarding the measured clot time as a function of life span for the optimized thrombin preparation, having been treated by 13.6% ethanol and 0.023 µM calcium chloride. As shown, the life span extends to 360 minutes and the clot time varies from 3 to 4 seconds.

Figure 10:
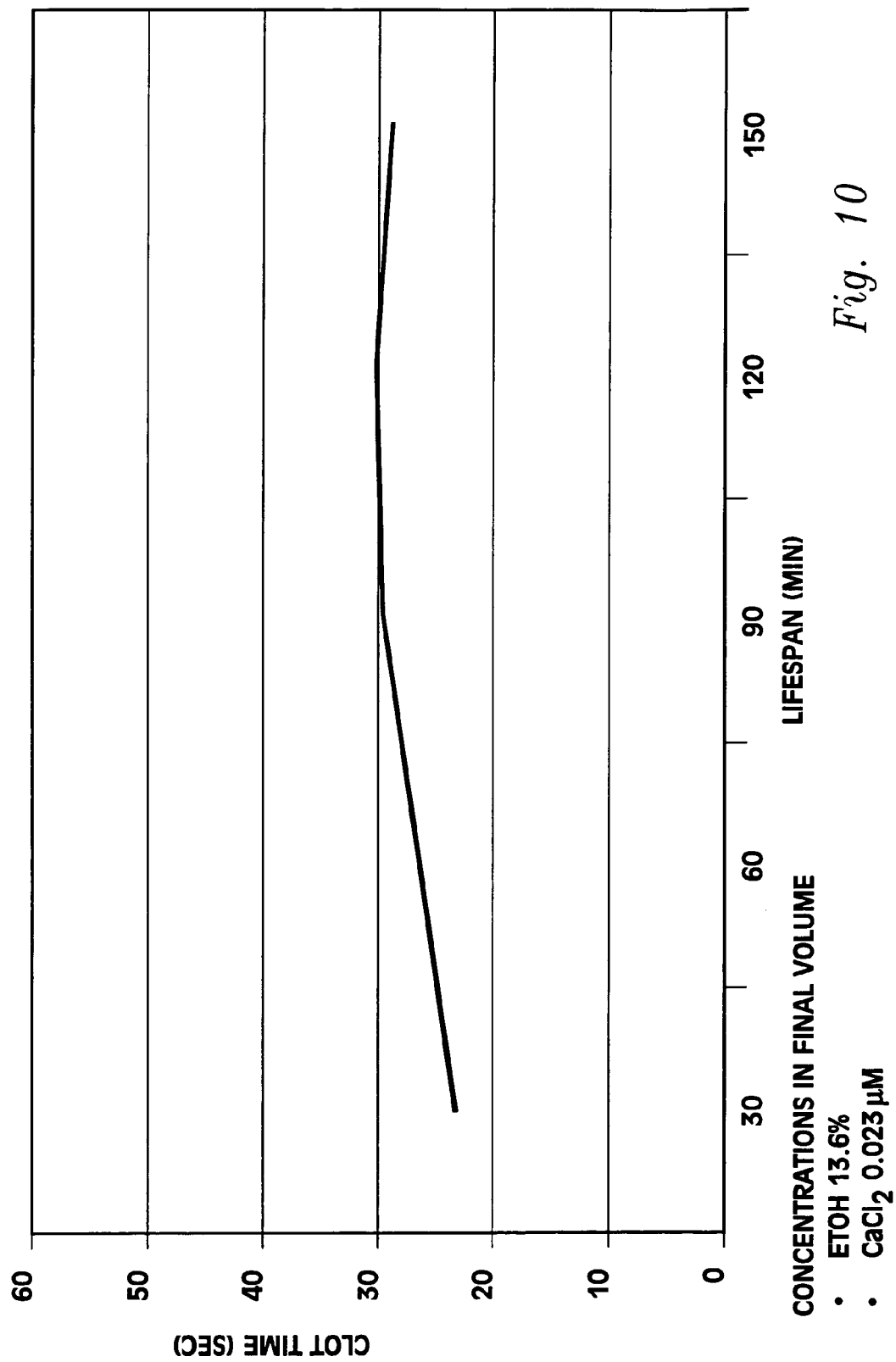
FIG. 10 is a view showing the life span of optimized thrombin preparation diluted at 1:15 with sterile saline for slow clotting.

FIG. 10 shows the effect of saline solution on the thrombin preparation optimized as in FIG. 9 with an ethanol concentration of 13.6% and a calcium chloride concentration of 0.023 µM as a function of life span. When the thrombin has been diluted 1 to 1.5 with saline, the clot time has been extended from just above 20 seconds to just less than 30 seconds, and has a life span of up to 150 minutes.

Figure 11:
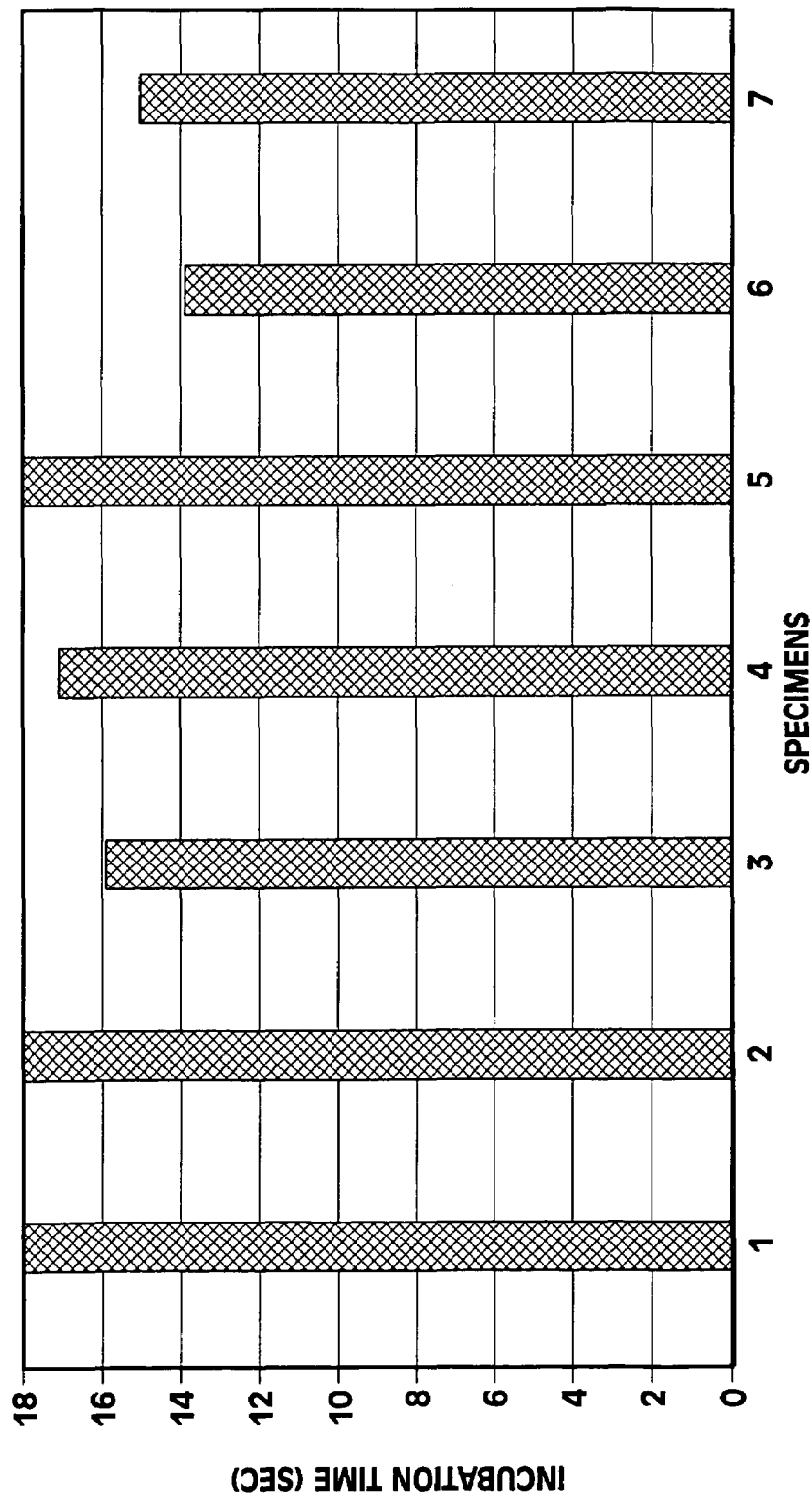
FIG. 11 is a chart illustrating the conversion/activation period required for the enrichment of a prothrombin fraction and its conversion to stable thrombin by mixture with a precise solution of EtOH and $CaCl_2$.

Referring to FIG. 11, there shown is the benefit in allowing the thrombin contained in the mixing syringe 26 to reside therein after agitation for almost 20 minutes in order to assure the effectiveness of the filtration step in removing particulate matter for subsequent utilization. The time span for conversion and activation allows enough particulate matter to be removed by the filter to optimize the use of the thrombin later in an narrow orificed dispenser, such as a sprayer or expressing through a thin tube.

Figure 12:
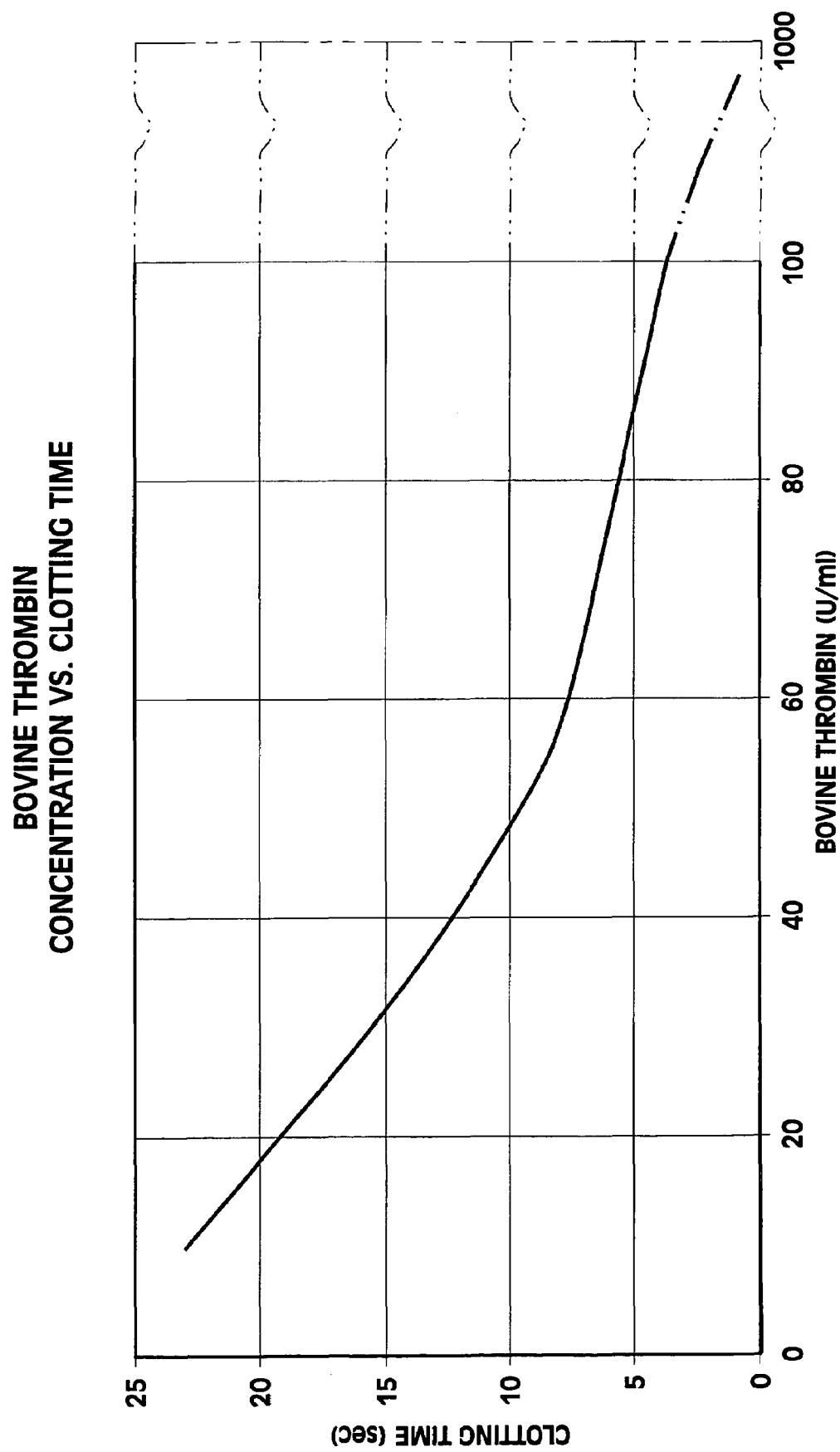
FIG. 12 is a chart illustrating thrombin (Bovine) concentrations (activity) as it relates to time of clotting.

FIG. 12 provides a prior art comparison of the activity of thrombin sourced from Bovine blood plasma as it relates to the speed of clotting, showing that autologous thrombin derived from this invention provides a clotting speed equivalent to 100 iu/mL of Bovine thrombin.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A thrombin composition free of fibrin clots, consisting essentially of
   Plasma;
   Ethanol (EtOH), wherein EtOH is present at a concentration between 8% and 18% by volume; and
   $CaCl_2$, wherein $CaCl_2$ is present at a concentration between 0.011 µM and 0.045 µM;
   whereby particulate matter in the composition has been substantially depleted by filtration.

2. The composition of claim 1 wherein ethanol is present at 13.6% by volume and $CaCl_2$ is present at 0.023 µM.

3. The composition of claim 1 wherein ethanol is present at 13.6% by volume.

4. The composition of claim 1 wherein $CaCl_2$ is present at 0.023 µM.

5. The composition of claim 1 wherein thrombin isolated from the composition has a clotting time of five seconds or less and is stable for more than 15 minutes.

6. The composition of claim 1 wherein thrombin isolated from the composition has a clotting time of five seconds or less and is stable for 240 minutes or greater.

7. The composition of claim 1 wherein thrombin isolated from the composition has a clotting time of twenty to thirty seconds and is stable for up to 150 minutes.

8. The composition of claim 1 wherein thrombin isolated from the composition has a clotting time of three to four seconds and is stable for up to 360 minutes.

9. The composition of claim 1 wherein said composition is prepared in a glass container.

10. The composition of claim 1 wherein thrombin isolated from the composition is diluted with saline to alter the clotting time.

11. A thrombin composition free of fibrin clots, consisting essentially of:
    Plasma;
    Ethanol (EtOH), wherein EtOH is present at a concentration between 8% and 18% by volume; and
    a source of calcium ions, wherein calcium ions are present at a concentration between 0.011 µM and 0.045 µM;
    whereby particulate matter in the composition has been substantially depleted by filtration.

12. The composition of claim 11 wherein ethanol is present at 13.6% by volume and calcium ions are present at 0.023 µM.

13. The composition of claim 11 wherein ethanol is present at 13.6% by volume.

14. The composition of claim 11 wherein calcium ions are present at 0.023 µM.

15. The composition of claim 11 wherein thrombin isolated from the composition has a clotting time of five seconds or less and is stable for more than 15 minutes.

16. The composition of claim 11 wherein thrombin isolated from the composition has a clotting time of five seconds or less and is stable for 240 minutes or greater.

17. The composition of claim 11 wherein thrombin isolated from the composition has a clotting time of twenty to thirty seconds and is stable for up to 150 minutes.

18. The composition of claim 11 wherein thrombin isolated from the composition has a clotting time of three to four seconds and is stable for up to 360 minutes.

19. The composition of claim 11 wherein said composition is prepared in a glass container.

20. The composition of claim 1 wherein thrombin isolated from the composition is diluted with saline to alter the clotting time.

* * * * *